(12) United States Patent
Roe

(10) Patent No.: US 7,288,573 B2
(45) Date of Patent: *Oct. 30, 2007

(54) METHOD OF REPELLING INSECTS

(75) Inventor: R. Michael Roe, Middlesex, NC (US)

(73) Assignee: North Carolina State University, Raleigh, NC (US)

( * ) Notice: Subject to any disclaimer, the term of this patent is extended or adjusted under 35 U.S.C. 154(b) by 292 days.

This patent is subject to a terminal disclaimer.

(21) Appl. No.: 10/486,632

(22) PCT Filed: Feb. 14, 2002

(86) PCT No.: PCT/US02/07620

§ 371 (c)(1),
(2), (4) Date: Jul. 23, 2004

(87) PCT Pub. No.: WO02/071840

PCT Pub. Date: Sep. 19, 2002

(65) Prior Publication Data

US 2004/0242703 A1 Dec. 2, 2004

Related U.S. Application Data

(63) Continuation-in-part of application No. 09/808,499, filed on Mar. 14, 2001, now Pat. No. 6,437,001.

(51) Int. Cl.
*A01N 35/02* (2006.01)
(52) U.S. Cl. ............... 514/675; 514/919; 424/DIG. 10; 504/101
(58) Field of Classification Search ............... 514/675, 514/919; 424/DIG. 10; 504/101
See application file for complete search history.

(56) References Cited

U.S. PATENT DOCUMENTS

| | | | | |
|---|---|---|---|---|
| 2,283,471 | A * | 5/1942 | Swaine | 514/688 |
| 3,474,176 | A * | 10/1969 | Freeman | 514/690 |
| 4,169,898 | A * | 10/1979 | Haase et al. | 514/675 |
| 4,388,352 | A * | 6/1983 | Allan et al. | 427/391 |
| 4,555,015 | A * | 11/1985 | Haase | 206/0.5 |
| 4,562,794 | A * | 1/1986 | Speckman | 119/651 |
| 4,775,532 | A * | 10/1988 | Clayton | 424/405 |
| 5,587,401 | A | 12/1996 | VanderMeer et al. | |
| 6,001,874 | A * | 12/1999 | Veierov | 514/533 |
| 6,258,857 | B1 * | 7/2001 | Iijima et al. | 516/1 |
| 6,437,001 | B1 * | 8/2002 | Roe | 514/675 |
| 6,676,955 | B2 * | 1/2004 | Kensek | 424/405 |
| 6,800,662 | B2 * | 10/2004 | Roe | 514/675 |
| 6,811,791 | B2 * | 11/2004 | Kensek | 424/406 |

FOREIGN PATENT DOCUMENTS

JP 9-30906 2/1997

WO WO 98/53678 12/1998

OTHER PUBLICATIONS

CAPLUS Abstract, STN Online, accession No. 1995:853240 (1995).*
CAPLUS Abstract, STN Online, accession No. 1989:419430 (1989).*
HCAPLUS abstract 1981:44430 (1981).*
HCAPLUS abstract 1999:308933 (1999).*
Sakata, Naohiro, et al., Abstract, Long-lasting insect repellents containing 2-undercanone and their mats, *Chemical Abstracts*, vol. 126, No. 16, pp. 189 (1997).
Du, et al., Electroantennogram and Oviposition Bioassay Responses of Culex quinquefasciatus and Culex tarsalis (Diptera: Culicidae) to Chemicals in Odors from Bermuda Grass Infusions, *Journal of Medical Entomology*, vol. 36, No. 2, pp. 158-166 (1999).
International Search Report for International Application Serial No. PCT/US02/07620 dated Sep. 26, 2002.
Linderman, Russell J., et al., Inhibition of Insect Juvenile Hormone Esterase by α,β-Unsaturated and α-Acetylenic Trifluoromethyl Ketones, *Pesticide Biochemistry and Physiology*, vol. 35, pp. 291-299 (1989).
Rochat, Didier, et al., Identification of Pheromone Synergists in American Palm Weevil, *Rhynchophorus palmarum*, and Attraction of Related Dynamis borassi, *J. Chem. Ecol*, vol. 26(1), pp. 155-187 (2000).
Renou, M., et al., Effects of Trifluoromethyl Ketones and Related Compounds on the EAG and Behavioural Responses to Pheromones in Male Moths, *Chem. Senses*, vol. 22(4), pp. 407-416 (1997).
Rosell, Gloria, et al., New Trifluoromethyl Ketones as Potent Inhibitors of Esterases: $^{19}$F NMR Spectroscopy of Transition State Analog Complexes and Structure-Activity Relationships, *Biochemical and Biophysical Research Communications*, vol. 226, pp. 287-292 (1996).
Yoshizawa, Takumi, et al., Attractancy of Some Methyl Ketones Isolated from Cheddar Cheese for Cheese Mites, *Bochu-Kagaku*, vol. 35(2), pp. 43-45 1970).
Szauman-Szumski, K.J., et al., Identification of chemicals attractive to the olive bark beetle, *Phloeotribus scarabaeoides*, in laboratory bioassays, vol. 43, pp. 345-355 (1998).
*Chemical Abstracts*, 125:208547, Abstracting JP 9-30906 (1997).
*CABA Abstract*, Accession No. 86:48796 (1985).

* cited by examiner

*Primary Examiner*—John Pak
(74) *Attorney, Agent, or Firm*—Myers Bigel Sibley & Sajovec, P.A.

(57) ABSTRACT

A method of repelling an insect pest such as a tick, mosquito or cockroach comprises applying to a subject or substrate, in an amount effect to repel the insect pest, a compound of Formula I:

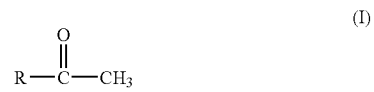

wherein R is C4-C20 linear or branched alkyl. Particularly preferred compounds of Formula (I) are 2-tridecanone and 2-undecanone.

20 Claims, 5 Drawing Sheets

METHOD OF REPELLING INSECTS

RELATED APPLICATIONS

The present application is the National Stage of International Application No. PCT/US02/07620, filed on 14 Mar. 2002 and published in English as PCT Publication No. WO 02/071840 on 19 Sep. 2002, which is a continuation-in-part commonly owned U.S. application Ser. No. 09/808,499, filed 14 Mar. 2001 (now U.S. Pat. No. 6,437,001), the disclosures of which are hereby incorporated herein by reference in its entirety.

FIELD OF THE INVENTION

The present invention concerns methods and formulations for repelling insects, particularly for repelling mosquitoes and ticks.

BACKGROUND OF THE INVENTION

Insect repellants are widely used throughout the United States and throughout the world. In some regions, the use of insect repellants is critical to avoiding or reducing the occurrence of disease carried by insects. For example the Centers for Disease Control (CDC) receives nearly 10,000 reports of Lyme disease (transmitted by deer ticks) and 1,000 reports of encephalitis (transmitted by mosquitoes) annually).

Currently, the most common insect repellent is N,N-diethyl-meta-toluamide (DEET). DEET was designed to be applicable to the skin of subjects, and is designed to repel rather than kill insects. Although in use for some time, concern has recently emerged about the potential toxicity of DEET to children. Recently the US Environmental Protection Agency (EPA) determined that it would no longer allow child safety claims on labels for DEET-containing products.

The United States EPA Facts: Methyl Nonyl Ketone (July 1995) describes methyl nonyl ketone as a dog and cat repellent/training aid and iris borer deterrent, but does not suggest its use as an insect repellent.

U.S. Pat. No. 2,283,471 to Swaine describes the use of compounds such as methyl nonyl ketone and methyl undecyl ketone as contact insecticides for aphids and similar piercing-sucking insects (all primitive plant-feeding insects) which require contact insecticides for their control, but does not suggest their use as insect repellents.

R. Linderman et al., *Pesticide Biochemistry and Physiology* 35, 291-299 (1989), describes the inhibition of insect juvenile hormone esterase by α,β-unsaturated and α-acetylenic trifluoromethyl ketones, but does not suggest the use thereof as insect repellents.

Accordingly, there remains a need for new ways to repel insects, particularly mosquitoes and ticks.

SUMMARY OF THE INVENTION

Accordingly, the present invention provides a method of repelling an insect pest, comprising applying to a subject or substrate, in an amount effect to repel the insect pest, a compound of Formula I:

wherein R is C4-C20 linear or branched alkyl, preferably linear and preferably C7 to C13 alkyl.

Particularly preferred insects for application of the present method are mosquitoes, ticks and cockroaches.

Further aspects of the present invention include compositions comprising compounds of Formula (I), or other active compounds, in combination with carriers or other ingredients for repelling insects, and the use of compounds of Formula (I) or active compounds disclosed herein for the preparation of a composition for repelling insects.

DETAILED DESCRIPTION OF THE PREFERRED EMBODIMENTS

Figure 1:
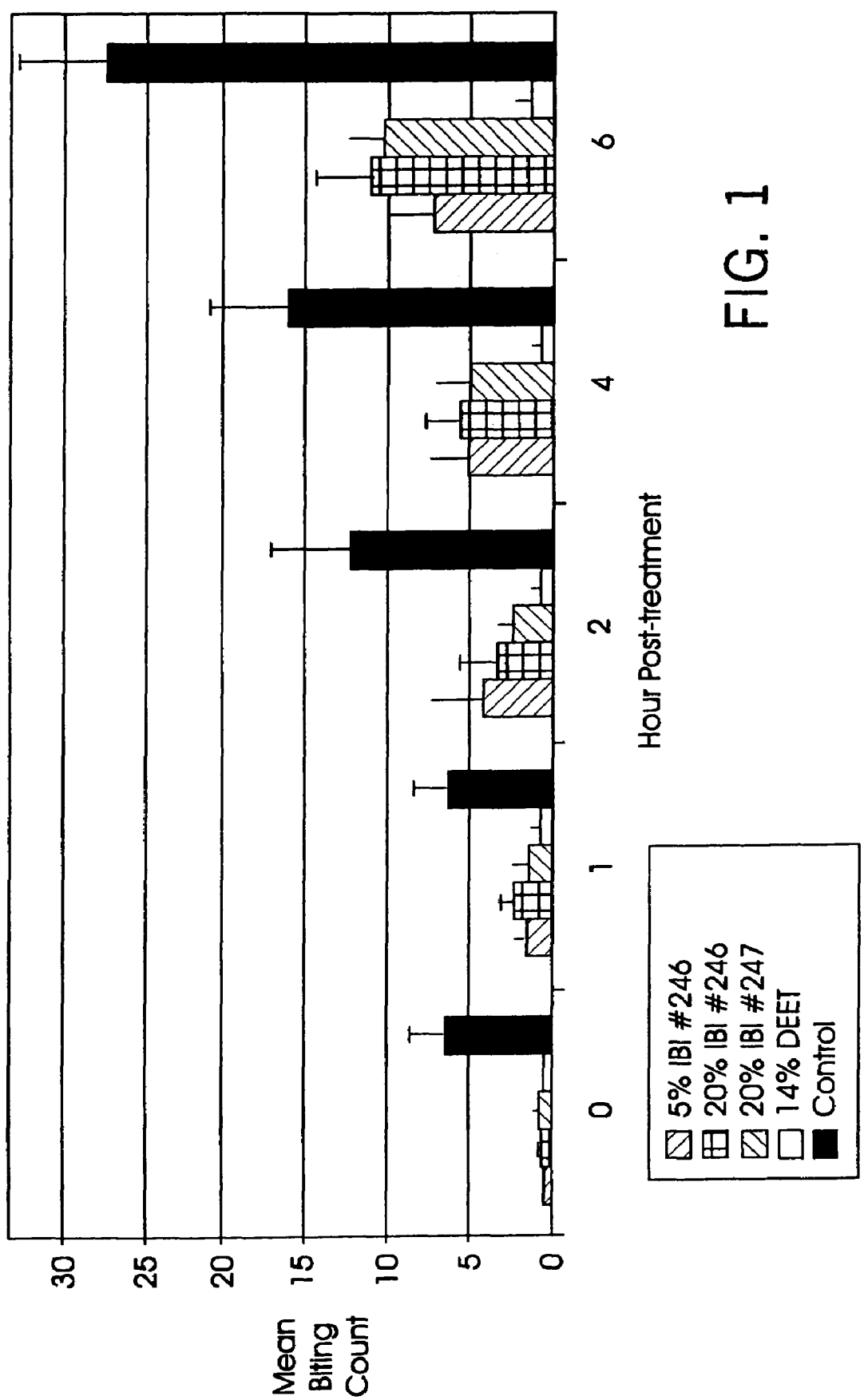
FIG. 1 presents the mean biting count and standard error by time interval post-treatment for *Culex quinquefasciatus* (Average biting count and standard error for three formulations (5% 2-undecanone (IBI-246), 20% 2-undecanone (IBI-246), 20% 2-tridecanone (IBI-247)) versus DEET and a non-treated control over five time intervals.

As used herein, the term "alkyl" (e.g., alkyl, alkylcarboxy, alkylphenyl, etc.) refers to a straight or branched chain hydrocarbon having from 4 to 20 carbon atoms, which alkyl may be linear or branched. The alkyl may optionally be substituted with substituents selected from the group which includes halo, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by a substituent selected from the group including alkyl, nitro, cyano, halo and lower perfluoroalkyl, multiple degrees of substitution being allowed. Examples of "alky" as used herein include, but are not limited to, n-butyl, n-pentyl, isobutyl, pentyl, hexyl, octyl, nonyl, undecyl, the like.

The term "loweralkoxy" as used herein means linear or branched $C_1$ to $C_4$ alkoxy, preferably methoxy, ethoxy, or propoxy.

The term "halo" as used herein means halogen, preferably fluoro, chloro, bromo or iodo, most preferably fluoro.

Subjects to be treated with compounds of the present invention include both human and animal subjects (e.g., dogs, cats, horses, cattle). Subjects may be directly or indirectly treated, such as by applying the active compound to the skin of the subject, or by applying the active compound to an article worn by or otherwise protecting the subject.

Substrates to be treated with compounds of the present invention include, but are not limited to, floors, plants, containers, walls, pools or open bodies of water, etc.

Insects that may be repelled by the methods of the present invention include ticks, fleas, cockroaches, and biting flies, typically of the order diptera, and further including mosquitoes, horse flies, deer flies, black flies, gnats, no-see ums, chiggers, etc.

The term "mosquito" as used herein concerns any type of mosquito (e.g., *Anopheles*, *Aedes*, and *Culex*), including but not limited to Tiger mosquitoes, *Aedes aboriginis*, *Aedes Aegypti*, *Aedes albopictus*, *Aedes cantator*, *Aedes sierrensis*, *Aedes sollicitans*, *Aedes squamiger*, *Aedes sticticus*, *Aedes vexans*, *Anopheles quadrimaculatus*, *Culex pipiens*, and *Culex quinquefaxciatus*.

The term "tick" as used herein includes any type of tick, including but not limited to, deer ticks, the American dog tick (*Dermacentor variabilis*), *Ornithodoros parkeri*, *O. moubata*, and *Dermacentor andersoni*.

The term "cockroach" as used herein refers to any type of cockroach, including but not limited to the American cockroach (*Periplaneta americana*), German cockroach (*Blattella germanica*), oriental cockroach (*Blatta orientalis*), wood cockroach (*Parcoblatta pennsylvanica*), brownbanded cockroach (*Supella longipalpa*), and smokybrown cockroach (*Periplaneta fuliginosa*).

Other insect that can be treated by the methods of the present invention include, but are not limited to: lice (Order Phthiraptera), such as head and body lice of humans, *Pediculus humanus capitis* and *P. H. humanus*; Fleas (Order Siphonaptera), such as cat and dog fleas, *Ctenocephalides* sp. human fleas, *Echidnophaga*, *Pulex* sp. Bees, wasps and ants (Order Hymenoptera) mites such as *Sarcoptes scabei* (human itch mite) the North American chigger or red bug, *Trombicula* sp. nematodes such as human parasitic nematodes, Silverfish (Order Thysanura), such as *Lepisma saccharina*, firebrat, *Thermobia domestica*; Termites (Order Isoptera) such as *Reticulitermes flavipes*, *Incisitermes minor*, *Marginitermes hubbardi*, and *Cryptotermes brevis*; Earwigs (Order Dermaptera); Psocids (Order Psocoptera) such as booklice; Beetles (Order Coleoptera), particularly wood eating beetles; Centipedes such as *Lithobius*, *Geophilus*, *Scutigera* and millipedes such as *Julus terrestris*; Scorpions such as *Centruroides sculpturatus* and *Mastigoproctus gianteus*; etc.

1. Repellant Compounds

Active compounds or compounds of Formula I herein are either known and may be produced in accordance with techniques known to those skilled in the art, or where novel may be produced by variations of known techniques which will be apparent to those skilled in the art.

2-tridecanone (methyl undecyl ketone) is commercially available from the Sigma-Aldrich Company, P.O. Box 2060, Milwaukee, Wis. 53201 USA as catalog number 17,283-9.

2-undecanone (methyl nonyl ketone) is commercially available from the Sigma-Aldrich Company, P.O. Box 2060, Milwaukee, Wis. 53201 USA as catalog number U-130-3.

2. Methods and Formulations for Repelling Insects

The present invention provides repellant compounds, compositions comprising said repellant compounds and the use of such repellant compounds and compositions in controlling pests, particularly insect pests such as mosquitoes.

Liquid formulations may be aqueous-based or non-aqueous (i.e., organic solvents), or combinations thereof, and may be employed as foams, gels, suspensions, emulsions, microemulsions or emulsifiable concentrates or the like. The ingredients may include rheological agents, surfactants, emulsifiers, dispersants or polymers.

In one embodiment, a floor wax composition may include repellant compounds as described herein, in an amount effective to repel cockroaches that might otherwise feed upon the composition once applied to floors, or to simply repel cockroaches from floor surfaces to which they are applied.

As will be appreciated by a person skilled in the art, the repellant concentration will vary widely depending upon the nature of the particular formulation, particularly whether it is a concentrate or to be used directly. The repellant compound will be present in the composition in a concentration of at least about 0.0001% by weight and may be 10, 50, 99 or 100% by weight of the total composition. The repellant carrier may be from 0.1% to 99.9999% by weight of the total composition. The dry formulations will have from about 0.0001-95% by weight of the pesticide while the liquid formulations will generally have from about 0.0001-60% by weight of the solids in the liquid phase.

The formulations may be applied to the subject's skin, or may be applied to garments, belts, collars, or other articles worn by the subject from whom insects are to be repelled. The formulation may be applied to netting or screening that protects a subject, particularly a sleeping subject. The formulations may be applied to non-animal substrates from which insects are to be repelled, such as plants. Application to subjects or substrates may be carried out by spraying, dusting, sprinkling or the like. It will be recognized that the concentration, applied amount and frequency of application will vary with the subject and locus of application, e.g., to the skin or hair of a human subject, skin or fur of a canine subject, etc. For topical application, the formulation may take the form of a spray formulation or a lotion formulation.

The compounds according to the present invention may be employed alone or in mixtures with one another and/or with such solid and/or liquid dispersible carrier vehicles as described herein or as otherwise known in the art, and/or with other known compatible active agents, including, for example, insecticides, acaricides, rodenticides, fungicides, bactericides, nematocides, herbicides, fertilizers, growth-regulating agents, etc., if desired, in the form of particular dosage preparations for specific application made therefrom, such as solutions, emulsions, suspensions, powders, pastes, and granules as described herein or as otherwise known in the art which are thus ready for use.

The repellant compounds may be administered with other insect control chemicals, for example, the compositions of the invention may employ various chemicals that affect insect behavior, such as insecticides, attractants and/or repellents, or as otherwise known in the art. The repellant compounds may also be administered with chemosterilants.

The repellant compounds are suitably applied by any method known in the art including, for example, spraying, pouring, dipping, in the form of concentrated liquids, solutions, suspensions, sprays, powders, pellets, briquettes, bricks and the like, formulated to deliver a repellant effective concentration of the repellant compound. The repellant formulations may be applied in a repellant effective amount to an area of pest infestation or an area susceptible to infestation, a body of water or container, a barn, a carpet, pet bedding, an animal, clothing, skin, and the like.

The following examples are illustrative of the practice of the present invention, and should not be construed as limiting thereof. All percentages are by weight and all solvent mixture proportions are by volume unless otherwise noted.

EXAMPLE 1

Mosquito Repellant

Untreated cheese cloth was wrapped around the right hand of a human subject and inserted into a cage of adult tiger mosquitoes (approximately 50 in the cage). The insects were immediately attracted to the subject's hand. The tiger mosquitoes were observed to be actively probing and biting the subject's hand through the cheese cloth within seconds. The subject was required to shake his hand violently to remove the insects from the cheese cloth when removing his hand from the cage, to avoid transferring the insects from the cage to the outside.

The same cheese cloth was then treated to saturation with a 1% by volume solution of 2-tridecanone/2-undecanone (approximately 50% by volume of each) in ethanol. The cloth was allowed to air dry to remove the ethanol.

After treatment as described above the cheese cloth was again wrapped around the subject's hand and placed in the same cage. Fewer (by 1/10) mosquitoes landed on the cheese cloth. This treatment was performed within five minutes of the control experiment described above. When mosquitoes did land on the cheese cloth, they were observed to remain thereon for only approximately 1 to 2 seconds and then fly off. No probing was observed, no bites were received, and the subject was able to easily remove his hand from the cage without risk of transferring mosquitoes.

EXAMPLE 2

Tick Repellant

A volume of 800 microliters of a 1% by volume solution of 2-undecanone and 2-tridecanone mix (50% each) in ethanol was added to one-half of a coarse 9 centimeter filter paper disc placed in a plastic petri plate of corresponding size and allowed to air dry. An exact control half filter paper disc was treated in a separate container with 800 microliters of ethanol at the same time. The control was allowed to air dry until no ethanol could be detected by smell approximately 2 centimeters from the surface of the filter paper. The treatment and ethanol control was then transferred to a sterile plastic petri plate containing 10 ticks, *Ornithodorus parkeri*. The control and treatment paper were positioned so that they covered most of the bottom of the plate but did not touch in the middle; they were separated by a distance of about 0.25 cm. The ticks were randomly distributed around the plate when the filter paper was introduced. Essentially 100% of the ticks were found on the ethanol control for 5 minutes through 3 hours. At three observation periods, 14 minutes, 1 hour and 2 hours, one tick was found at the margin between the two treatments. The experiment was run at room temperature and in the dark. Observations were made in normal laboratory light and took only a few seconds.

EXAMPLE 3

Mosquito Repellency of Undecanone

Forty milliliters of a 2.5 percent solution of undecanone in absolute ethanol was added to a gauze glove (20×15 centimeters) in a 250 milliliter beaker. After soaking for 1 minute, the glove was laid onto aluminum foil in a fume hood for 13 minutes and then suspended by one end from the sash of the fume hood for 3 minutes. The ethanol appeared to be completely evaporated after this treatment as determined by touch. Upon touch, the glove did not feel wet or cool. The same treatment was used without undecanone as a control. After the same drying steps, no odor of ethanol could be detected by smell. The control glove was the same physical dimensions and made from the same batch of material as the treatment. The control experiments including wetting and drying of the glove was conducted prior to the undecanone treatment.

Approximately 100 adult male and female mosquitoes (*Aedes taeniorhynchus*) (exact sex ratio not determined) were placed in a 12×12×14.5 inch stainless steel screened cage. The cage was fitted with a cloth stocking on one side to allow material to be added and removed from the cage by hand without allowing the mosquitoes to escape. The mosquitoes were added to the cage approximately 12 hours before the test. Two 1 ounce plastic cups containing 2-3 KIM WIPES™ brand paper wipes wetted with 20% sucrose in water were placed into the cage for a source of food and water. The insects were held over night for acclimation at 27 degrees Centigrade, 14:10 LD cycle and 50% relative humidity. The next morning, a few mosquitoes were seen resting on the sucrose feeding stations.

The following data are the control responses when the tester's hand covered by the ethanol treated (dried) glove was placed into the mosquito cage (at room temperature) for 20 seconds at the times indicated: 0 minutes, 10 landings and 1 bite; 10 minutes, 9-12 landings and 1 bite; 20 minutes, approximately 13 landings and no bites; and 40 minutes, approximately 13 landings and no bites. As soon as the tester's hand entered the cage, the mosquitoes demonstrated obvious host seeking behavior which including flying around the cage and in the near region of the tester's hand. However, only sustained landings of about 5 seconds were recorded as a positive response along with actual bites. After the conclusion of the control experiments, the tester's hand covered by the undecanone treated (dried) glove was placed into the mosquito cage (at room temperature) for 20 seconds at the times indicated: 0 minutes, 15 minutes, 25 minutes, 50 minutes, 1 hour and 40 minutes, 2 hours and 40 minutes, 3 hours and 40 minutes, and 4 hours and 40 minutes. No landings and no bites were noted at any of these time points. During the first 3 to 4 hours, the mosquitoes demonstrated no host seeking behavior, such as even trying to fly toward the tester's hand.

In conclusion, under the treatment conditions described above, undecanone was effective as a mosquito repellent for greater than 4 hours and 40 minutes.

EXAMPLE 4

Cockroach Repellency of 2-Undecanone

A commercially available paste floor wax is combined with one percent by weight of 2-undecanone and the two ingredients mixed thoroughly together. The paste floor wax is then applied to a region of flooring and buffed. The same paste floor wax, without 2-undecanone, is applied to an adjacent region of flooring in the same amount and also buffed. When released onto each region of flooring, cockroaches are found to spend less time in the region containing 2-undecanone than in the control region that does not contain 2-undecanone.

EXAMPLE 5

Mosquito Repellency of 2-Undecanone

Two mosquitoes cages were constructed using wood framing and fine mesh wire screen. The dimensions of each cage were 59 cm high×55 cm wide×59 cm deep. A hinged access door was installed at the front of each chamber for insertion of the water-filled containers filled with mosquito pupae. Also present at the front of each chamber was a 9 cm diameter plastic tube (i.d.) for insertion of the arm of the investigator. The arm insertion tube was sealed with a rubber stopper when not in use.

Mosquitoes (*Culex* spp.) were obtained (as pupae) from Carolina Biological Supply Co., Burlington, N.C., USA. Following their arrival, the mosquitoes were divided into approximately equal numbers in two water-filled containers and placed in the two cages described above. Some of the mosquitoes had hatched upon arrival.

Testing was done with 2-undecanone for repellent activity by treating one arm of the investigator with approximately 1 ml of the test solution. Following several minutes for solvent evaporation, the treated arm was inserted through the insertion tube for 5 minutes. The other arm was treated with ethanol (control) or a different concentration of 2-undecanone, and inserted into the insertion tube of the adjacent chamber. Next, the behavior of the mosquitoes in response to the presence of the investigator's arms was noted. Mosquito behavior was recorded as 1) landing or attempting to land on the investigator's arm, versus 2) dispersal away from the treated arm towards the opposite ends of the cage. The approximate number of mosquitoes present at the beginning of the observations was noted. The observations were repeated (without re-treatment of the investigator's hand and arm) after 3 hours and again after 6 hours. Treatments were alternated between the different cages. Each observation was repeated 3 times. Tests were done with 20%, 5%, 2%, 0.5% 2-undecanone, 20% DEET, and the ethanol control.

The results are summarized in Table 1. With one exception, none of the mosquitoes succeeded in biting, although mosquitoes that landed on the investigator's arm were dislodged by flicking the arm or hand. In most cases, any physical movement of the hand or arm will induce the mosquito to leave. Thus, few if any bites were expected. Landings on the arm were considered as evidence of attraction, with intent to bite. Mosquitoes flying near the arm were not recorded, although such activity was noted in the comments in Table 1.

At the 0.5% concentration of 2-undecanone, no differences between the treated arm and the ethanol controls were observed, although the number of landings on the treated arm was less than with the ethanol control.

Following insertion of the arm treated with the 2% concentration, many of the mosquitoes dispersed to the sides and opposite end of the cage. However, others were flying nearby and there were 2 landings. When repeated at three hours after treatment, there was no effect.

Following insertion of the arm treated with the 5% concentration, there was immediate and obvious repellent behavior. All of the mosquitoes dispersed to the opposite side and end of the cage. There were no landings and none were flying near the treated arm. The effect was similar at 3 hours after treatment. Again, there were no landings, although some mosquitoes remained active. The effect was absent after 6 hours.

Following insertion of the arm treated with the 20% concentration, all of the mosquitoes immediately dispersed to the opposite side and end of the cage and remained against the wire screen. None were flying and there were no landings. The effect was similar at 3 hours after treatment, i.e., there was no mosquito activity and no landings. However, the effect was lost after 6 hours.

Following insertion of the arm treated with DEET, most mosquitoes dispersed rapidly away from the arm, although some continued flying. They did not all stay on the wire screen. However, there were no landings and none remained in the vicinity of the treated arm. The effect persisted after 3 hours, but was largely lost after 6 hours.

The results show that 2-undecanone is repellent for mosquitoes, with the strongest effect at the 5% and 20% concentrations. The most impressive evidence of this repellent effect was the observation that the mosquitoes immediately disperse away from the treated arm and actually stop flying, instead lining up on the wire screen of the cage. That the mosquitoes are still alive is indicated by the observation that they resume flying hours later.

The adult mosquito population in the cages declined during the course of the experiment, even though water-filled containers with numerous late stage larvae and pupae were present to generate fresh adults. Consequently, the numbers of flying adults were not exactly the same for all of the treatments.

TABLE 1

Summary of test observations for repellent activity of 2-undecanone against mosquitoes.

| | Hours after treatment | | | | | |
|---|---|---|---|---|---|---|
| | 0 hours | | 3 hours | | 6 hours | |
| Replicate No. | No. landings | No. Present | No. landings | No. present | No. Landings | No. present |
| 1.1. Ethanol Control | | | | | | |
| 1 | 3 | 45 | 1 | 43 | 1 (bite) | 35 |
| 2 | 2 | 41 | 0 | 41 | 0 | 40 |
| 3 | 4 | 40 | 2 | 33 | 2 | 27 |
| 4 | 2 | 27 | 4 | 23 | 3 | 25 |
| 5 | 1 | 18 | 0 | 25 | 3 | 21 |
| Mean | 2.4 | | 5.0 | | 1.8 | |
| 1.2. 0.5% Undecanone | | | | | | |
| 1 | 1 | 18 | 1 | 15 | 0 | 16 |
| 2 | 0 | 16 | 0 | 14 | 1 | 15 |
| 3 | 1 | 17 | 1 | 12 | 0 | 17 |
| Mean | 0.7 | | 0.7 | | 0.3 | |
| Comments: Most mosquitoes were very active, flying indiscriminately throughout the cage. No obvious avoidance, no dispersal away from the treated arm. | | | | | | |
| 1.3. 2% Undecanone | | | | | | |
| 1 | 1 | 23 | 1 | 18 | 1 | 15 |
| 2 | 1 | 20 | 2 | 17 | 1 | 15 |
| 3 | 0 | 17 | 0 | 18 | 0 | 13 |
| Mean | 0.7 | | 1.0 | | 0.7 | |
| Comments: At this concentration, many of the mosquitoes dispersed to the opposite side of the cage, others were flying about in the vicinity of the treated arm, and others remained inactive. After 3 hours, no repellent behavior was evident. All of the mosquitoes were flying about indiscriminately. | | | | | | |

TABLE 1-continued

Summary of test observations for repellent activity of 2-undecanone against mosquitoes.

| | Hours after treatment | | | | | |
|---|---|---|---|---|---|---|
| | 0 hours | | 3 hours | | 6 hours | |
| Replicate No. | No. landings | No. Present | No. landings | No. present | No. Landings | No. present |
| 1.4. 5% Undecanone | | | | | | |
| 1 | 0 | 35 | 0 | 32 | 1 | 22 |
| 2 | 0 | 32 | 0 | 30 | 1 | 23 |
| 3 | 0 | 32 | 0 | 30 | 1 | 24 |
| Mean | 0 | | 0 | | 1.0 | |

Comments: The formulation was highly repellent. Mosquitoes immediately dispersed to the far sides of the cage, away from the treated arm. None were observed flying near or towards the treated hand and arm. Most of the mosquitoes remained on the wire screen. This effect persisted even after 3 hours, with only a slight increase in mosquito activity, but the effect was no longer apparent after 6 hours.

1.5. 20% Undecanone

| 1 | 0 | 12 | 0 | 12 | 0 | 7 |
|---|---|---|---|---|---|---|
| 2 | 0 | 10 | 0 | 9 | 0 | 5 |
| 3 | 0 | 10 | 0 | 8 | 0 | 5 |
| Mean | 0 | | 0 | | 0 | |

Comments: The formulation was highly repellent. Mosquitoes immediately dispersed to the far sides of the cage, away from the treated arm. Effect was extremely rapid. None were observed flying near or towards the treated hand and arm. All of the mosquitoes remained on the wire screen. This effect persisted at 3 hours without change. By 6 hours, some mosquito activity was apparent, but no landings occurred.

1.6. DEET Control

| 1 | 0 | 23 | 0 | 28 | 1 | 25 |
|---|---|---|---|---|---|---|
| 2 | 0 | 19 | 0 | 27 | 0 | 30 |
| 3 | 0 | 27 | 0 | 32 | 0 | 35 |
| Mean | 0 | | 0 | | 0.3 | |

Comments: DEET was highly repellent. Mosquitoes tended to disperse to the far sides of the cage, away from the treated arm. None were observed flying near or towards the treated hand and arm. However, some were still flying. This effect was similar after 3 hours. By 6 hours, most mosquitoes were actively flying, even though few approached the treated arm or landed.

EXAMPLE 6

Mosquito Repellency of 2-Undecanone and 2-Tridecanone

Cages. The same two mosquitoes cages described in Example 5 were used for this example. The cages were constructed using wood framing and fine mesh wire screen. The dimensions of each cage were 59 cm high×55 cm wide by 59 cm deep. A hinged access door was installed at the front of each chamber for insertion of the water-filled containers filled with mosquito pupae. Also present at the front of each chamber was a 9 cm diameter plastic tube (i.d.) for insertion of the arm of the investigator. The arm insertion tube was sealed with a rubber stopper when not in use.

Mosquitoes and Mosquito Rearing. Mosquitoes (*Culex* spp.) were obtained (as pupae and larvae) from Carolina Biological Supply Co., Burlington, N.C., USA in two successive shipments, so as to provide a continuing long term supply of fresh insects. Following their arrival, the mosquitoes were divided into approximately equal numbers in multiple water-filled containers and placed in the two cages described above. The larval and pupal cultures were fed with insect rearing compound. In addition, the water was changed regularly by filtration to minimize contamination and prevent overcrowding. Continuous culturing made it possible to increase the mosquito numbers to more than 100 insects per cage.

Test Compounds and Testing Schedule. Testing was done with two compounds, 2-undecanone, and 2-tridecanone, for repellent activity by treating one arm of the investigator with approximately 1 ml of the test solution. Following several minutes for solvent evaporation, the treated arm was inserted through the insertion tube for 5 minutes. The other arm was treated with isoprbpanol (control) or a different concentration of the compound, and inserted into the insertion tube of the adjacent chamber. Next, the behavior of the mosquitoes in response to the presence of the investigator's arms was noted. Mosquito behavior was recorded as 1) landing or attempting to land on the investigator's arm, or coming to rest on the wire screen immediately adjacent to the investigator's arm or hand, versus 2) dispersal away from the treated arm towards the opposite ends of the cage. The approximate number of mosquitoes present at the beginning of the observations was noted. For treatments with 2-undecanone, observations were made initially to confirm 100% repellent activity of the compound immediately after treatment but observations were not recorded. Recording of efficacy was delayed until 6 hours after treatment, and then repeated at 12 and 24 hours post-treatment. For treatment with 2-tridecanone, the observations commenced immediately after solvent drying; then, the observations were repeated (without re-treatment of the investigator's hand and arm) after 6 hours, 12 hours and 24 hours. Treatments were alternated between the different cages. Each observation was repeated 3 times.

2-tridecanone was obtained as a solid. To prepare this compound for testing, it was subjected to gentle heating in a 37° C. water bath to liquefy it, and aliquots of the stock were diluted volume: volume with isopropanol to 50% concentration and 20% concentration. Sufficient pure compound was retained for direct application (undiluted).

Tests were done at concentrations of 100%, 50%, and 20% for each of the two compounds, as well as 20% DEET, and the isopropanol control.

Observations. Mosquitoes were recorded as 1) repelled if they dispersed away from the treated hand/arm, changed course while in flight after approaching the treated hand/arm, or failed to land on the wire screen adjacent to the treated hand/arm; 2) not repelled if they attempted to land on the treated hand/arm, did not change course in flight and/or came to rest on the wire screen of the cage adjacent to the treated hand/arm.

Results. Testing commenced immediately after arrival of the mosquitoes, and continued over a three week observation period with freshly hatched mosquitoes that emerged from pupae held in water containers in the cages. Thus the cages served as emergence containers, thereby allowing a gradual increase in the number of mosquitoes for testing. As a result, some tests were done with smaller numbers of mosquitoes present than in other tests.

The results are tabulated in Table 2. The isopropanol controls established the base-line averages for use in comparing repellent activity, with means of 12.0, 14.7, 18.2 and 14.3 mosquitoes, respectively, landing on or near the treated hand/arm at the four different time intervals. On a percentage basis, this represented 12.0, 13.3, 16.7 and 13.1%, or a grand average of 14.3%.

Table 3 presents the efficacy found at the different time intervals for each of the compounds at the three different concentrations and for DEET. Efficacy was calculated according to the formula: [(no. landings/no. present in control)−(no. landings/no. present in experimental) divided by (no. landings/no. present in control)]×100.

2-undecanone. At time 0 post-treatment, all three concentrations showed 100% repellent activity, i.e., there were no landings on or adjacent to the treated hand/arm. Consequently, the zero time is omitted from this part of Table 2.

For the 100% concentration, residual repellent activity was observed at 6 hours post-treatment. There were no landings or mosquitoes on the wire screen near the treated hand/arm. Thus, repellent activity was 100% at 6 hours post-treatment for this compound. Avoidance/repellent behavior was much weaker after 12 hours (8.6%) and absent after 24 hours post-treatment.

For the 50% concentration, strong residual repellent activity was observed at 6 hours (1.1%), and considerably weaker was observed at 12 hours (5.8%) or 24 hours (5.7%).

For the 20% concentration, there was repellent activity at 6 hours (2.5%) but no residual activity after 12 hours (17.1%) and 24 hours (13.4%).

Table 2 shows the efficacy of repellent activity for 2-undecanone derived from these data. For the 100% concentration, residual activity was 100% at 6 hours and some repellent activity was still evident after 12 hours. This was more effective than DEET for the comparable periods. At the 50% concentration, residual activity was still very strong at 6 hours and again at 12 hours and even 24 hours. In all cases, residual activity was greater than that observed with DEET. At the 20% concentration, some residual activity was still evident at 6 hours but none thereafter.

Following insertion of the hand/arm treated with any of the three concentrations, all of the mosquitoes dispersed to the sides and opposite end of the cage and collected on the wire screen. When disturbed by banging on the sides of the cage, some mosquitoes would take flight but quickly fled from the treated subject and accumulated on the wire screens. None would fly more than a few seconds. This effect persisted for 6 hours at all three concentrations, but declined or was lost after 12 hours.

2-tridecanone. Observations with this compound were recorded for the zero time period, as well as 6, 12 and 24 hours post-treatment.

For the 100% concentration, there was strong repellent activity immediately after treatment (0 hours) with only 1.8% of the mosquitoes landing nearby, but little or no residual repellent activity at 6 hours and 12 hours, and none after 24 hours. For the 50% concentration, again there was very strong repellent activity, with only 0.7% landings. Thereafter, some residual repellent activity was observed at 6 hours with 4.3% mosquito contacts or landings, but no residual activity at 12 or 24 hours. For the 20% concentration, repellant activity was not observed.

Table 3 shows the efficacy of repellent activity for 2-tridecanone derived from these data. For the 100% concentration, there was strong repellent activity immediately after treatment (87.7%), but residual activity was very weak or absent at 6 hours. The calculated increase at 12 hours is an anomaly that may reflect differences in the means for the controls (13.3 at 6 hours versus 16.7 at 12 hours). For the 50% concentration, efficacy was strong immediately after treatment and there was some residual activity after 6 hours, comparable to that seen with DEET. However, there was no residual activity after 12 and 24 hours. For the 20% concentration, repellant activity was not observed.

DEET. This compound, applied as a 20% spray, showed strong immediate and residual activity for up to 6 hours, weak activity at 12 hours and none thereafter.

Discussion. The results indicate that the 2-undecanone and 2-tridecanone are repellent for mosquitoes. Of the two different compounds, 2-undecanone showed the greatest activity overall. Following insertion of the hand/arm treated with this compound, the mosquitoes immediately dispersed towards the opposite sides of the cage and actually stop flying, instead lining up on the wire screen of the cage. 2-undecanone also showed very strong residual activity at 6 hours and weak but evident repellent activity at 12 hours post-treatment when applied at the 100% and 50% concentrations. At 50%, activity was even seen at 24 hours. At these concentrations, activity was greater than for 20% DEET. When applied at the 20% concentration, 2-undecanone showed residual repellent activity at 6 hours, although less than that found with 20% DEET. However, there was no residual activity after 12 and 24 hours.

The results for 2-tridecanone show that this compound is less effective as a repellent against mosquitoes than 2-undecanone. Although effective when applied at 50% or 100% concentrations immediately after treatment, there was limited residual activity. Activity was not observed for 20% concentration.

2-undecanone dispersed easily on the skin and had a pleasant odor. At 100%, white deposits appeared after drying, but flaked off within a few hours. 2-tridecanone is a solid at room temperature and, consequently, was more difficult to apply. It left a slightly pungent, mildly unpleasant odor that disappeared within 6 hours.

The adult mosquito population in the cages increased greatly during the 2½ week study period. Consequently, some observations were repeated in order to take advantage of the greater numbers present. This is reflected in the increased number of replicates for 2-undecanone at 50% concentration and in the isopropanol controls.

TABLE 2

Summary of test observations for repellent activity of 2-undecanone and 2-tridecanone against mosquitoes.

| | Hours after treatment | | | | | | | |
|---|---|---|---|---|---|---|---|---|
| | 0 hours | | 6 hours | | 12 hours | | 24 hours | |
| Replicate No. | No. landings | No. present | No. landings | No. present | No. landings | No. present | No. landings | No. present |
| 2.1. Isopropanol Control | | | | | | | | |
| 1 | 13 | 77 | 16 | 118 | 8 | 69 | 19 | 134 |
| 2 | 14 | 83 | 18 | 123 | 19 | 133 | 14 | 82 |

TABLE 2-continued

Summary of test observations for repellent activity of 2-undecanone and 2-tridecanone against mosquitoes.

| 3 | 12 | 89 | 12 | 125 | 21 | 135 | 11 | 122 |
| 4 | 11 | 80 | 13 | 110 | 22 | 105 | 13 | 97 |
| 5 | 10 | 76 | 15 | 98 | 22 | 111 | 13 | 111 |
| 6 | 12 | 88 | 14 | 89 | 17 | 99 | 16 | 110 |
| Mean | 12.0 | 82.2 | 14.7 | 110.5 | 18.2 | 108.7 | 14.3 | 109.3 |
| Percent | 14.6% | | 13.3% | | 16.7% | | 13.1% | |

Percent = [(No. landings/No. present)] × 100

| | Hours after treatment | | | | | |
| --- | --- | --- | --- | --- | --- | --- |
| | 6 hours | | 12 hours | | 24 hours | |
| Replicate No. | No. landings | No. present | No. landings | No. present | No. landings | No. present |

2.2. 100% 2-Undecanone

| 1 | 0 | 21 | 3 | 19 | 3 | 18 |
| 2 | 0 | 19 | 1 | 19 | 3 | 14 |
| 3 | 0 | 20 | 1 | 21 | 3 | 15 |
| Mean | 0 | 20 | 1.7 | 19.7 | 3.0 | 15.7 |
| Percent | 0% | | 8.6% | | 19.1% | |

Comments: Strong avoidance response was still evident at 6 hours. Avoidance was much weaker after 12 hours and no obvious avoidance, no dispersal away from the treated arm was observed by 24 hours.

23. 50% IBI-246

| 1 | 0 | 23 | 1 | 18 | 3 | 15 |
| 2 | 0 | 20 | 2 | 17 | 2 | 15 |
| 3 | 0 | 17 | 2 | 18 | 2 | 17 |
| 4 | 1 | 118 | 13 | 123 | 11 | 115 |
| 5 | 3 | 110 | 13 | 93 | 16 | 116 |
| 6 | 4 | 65 | 12 | 105 | 11 | 119 |
| Mean | 1.3 | 58.8 | 7.2 | 124.7 | 7.5 | 132.3 |
| Percent | 2.2% | | 5.8% | | 5.7% | |

Comments: At this concentration, virtually all of the mosquitoes dispersed to the opposite sides of the cage away from the treated arm/hand, and none were flying about in the vicinity of the treated arm even after 6 hours post-treatment. However, after 12 hours, no repellent behavior was evident. All of the mosquitoes were flying about indiscriminately.

2.4. 20% 2-Undecanone

| 1 | 0 | 29 | 5 | 37 | 4 | 32 |
| 2 | 0 | 27 | 6 | 28 | 4 | 29 |
| 3 | 2 | 28 | 4 | 23 | 4 | 26 |
| Mean | 0.7 | 28.0 | 5.0 | 29.3 | 4.0 | 29.0 |
| Percent | 7.1% | | 17.1% | | 13.8% | |

Comments: Strong repellent activity was observed even after 6 hours, similar to that observed with the 50% treatment. However, after 12 hours, no repellent behavior was evident. All of the mosquitoes were flying about indiscriminately.

| | Hours after treatment | | | | | | | |
| --- | --- | --- | --- | --- | --- | --- | --- | --- |
| | 0 hours | | 6 hours | | 12 hours | | 24 hours | |
| Replicate No. | No. landings | No. present | No. landings | No. present | No. landings | No. present | No. landings | No. present |

2.5. 100% 2-Tridecanone

| 1 | 0 | 66 | 9 | 85 | 16 | 110 | 17 | 112 |
| 2 | 1 | 73 | 10 | 90 | 7 | 105 | 15 | 115 |
| 3 | 3 | 74 | 10 | 93 | 8 | 103 | 13 | 111 |
| Mean | 1.3 | 71.0 | 9.7 | 89.3 | 10.3 | 106.0 | 15.0 | 112.7 |
| Percent | 1.8% | | 10.9% | | 9.7% | | 13.3% | |

Comments: The compound was highly repellent. A huge cloud of mosquitoes retreated rapidly to the far sides of the cage, away from the treated arm. None were observed flying near or towards the treated hand and arm. Most of the mosquitoes remained on the wire screen. However, no residual activity was observed. Repellent effect was lost by 6 hours. The compound was mildly irritating when applied at full strength, and left white deposits on skin.

2.6. 50% 2-Tridecanone

| 1 | 0 | 27 | 3 | 36 | 7 | 32 | 7 | 29 |
| 2 | 1 | 29 | 0 | 26 | 4 | 25 | 4 | 26 |
| 3 | 1 | 31 | 1 | 29 | 6 | 30 | 4 | 25 |

TABLE 2-continued

Summary of test observations for repellent activity of
2-undecanone and 2-tridecanone against mosquitoes.

| | | | | | | | | |
|---|---|---|---|---|---|---|---|---|
| Mean | 0.7 | 29.0 | 1.3 | 30.3 | 5.7 | 29.0 | 5.0 | 26.7 |
| Percent | 2.4% | | 4.3% | | 19.7% | | 18.7% | |

Comments: The compound showed strong residual repellent activity after 6 hours, but activity greatly diminished or was absent after 12 and 24 hours.

2.7. 20% 2-Tridecanone

| | | | | | | | | |
|---|---|---|---|---|---|---|---|---|
| 1 | 4 | 27 | 3 | 34 | 3 | 36 | 5 | 39 |
| 2 | 3 | 28 | 4 | 34 | 5 | 37 | 6 | 38 |
| 3 | 5 | 28 | 7 | 33 | 6 | 36 | 6 | 38 |
| Mean | 4.0 | 27.7 | 4.7 | 33.7 | 4.7 | 36.3 | 5.7 | 38.3 |
| Percent | 14.4% | | 14.0% | | 13.0% | | 14.9% | |

Comments: No residual repellent activity was observed.

2.8. DEET CONTROL

| | | | | | | | | |
|---|---|---|---|---|---|---|---|---|
| 1 | 2 | 93 | 10 | 121 | 12 | 130 | 14 | 122 |
| 2 | 0 | 111 | 4 | 118 | 15 | 133 | 14 | 127 |
| 3 | 2 | 96 | 3 | 120 | 18 | 131 | 11 | 109 |
| Mean | 1.3 | 100 | 5.7 | 119.7 | 15.0 | 131.3 | 13.0 | 119.3 |
| Percent | 1.3% | | 4.8% | | 11.4% | | 10.9% | |

Comments: DEET was highly effective with strong residual activity persisting 6 hours after treatment, but no residual activity was observed at 12 or 24 hours post-treatment.

TABLE 3

Repellent efficacy of 2-undecanone and 2-tridecanone at three
different concentrations and 20% DEET against mosquitoes.
Percent Efficacy Post-Treatment

| Compound | 0 hours | 6 hours | 12 hours | 24 hours |
|---|---|---|---|---|
| 2-undecanone - 100% | 100% | 100% | 48.5% | 0% |
| 2-undecanone - 50% | 100% | 83.5% | 65.3% | 56.5% |
| 2-undecanone - 20% | 100% | 46.6% | 0% | 0% |
| 2-tridecanone - 100% | 87.7% | 18.1% | 41.9% | 0% |
| 2-tridecanone - 50% | 95.2% | 67.7% | 0% | 0% |
| 2-tridecanone - 20% | 1.5% | 0% | 22.2% | 0% |
| DEET - 20% | 91.1% | 63.9% | 31.7% | 16.8% |

EXAMPLE 7

Mosquito Repellency of 2-Undecanone and 2-Tridecanone

This experiment was performed to evaluate the comparative repellency of 5% and 20% 2-undecanone in ethanol, 20% 2-tridecanone in isopropanol and Off!™ 14.25% DEET Insect Repellent aerosol against *Aedes albopictus* (Asian tiger mosquitoes) and *Culex quinquefasciatus* (southern house mosquitoes).

Materials and Methods

Three to four-day-old laboratory-reared female *Ae. albopictus* and *Cx. quinquefasciatus* were transferred by aspiration into eight cages measuring 10 inches high×10 inches wide×13 inches deep at a targeted stocking rate of 100 and 200, respectively. Four cages contained *Ae. albopictus* and four contained *Cx. quinquefasciatus*. A greater number of *Cx. quinquefasciatus* was used to compensate for lower biting activity anticipated for this species. The number dead, escapees and recovery at end of the study are presented in Table 4. The actual number of females per cage was lower than the target-stocking rate because of the high number of males that were inadvertently introduced into the cages. Each cage contained a screened back wall, clear Plexiglas top, stockinette entry sleeve and solid aluminum floor and sidewalls. The mosquitoes were fed water and sugar water prior to and between tests. The tests were conducted over four days, Aug. 7-10, 2001, with four men participating as testers. All testers washed both arms with a non-fragrance soap, rinsed and swabbed with 25% ethanol prior to applying treatments. Treatments were applied to the forearm in a region extending from the wrist to a point measured at 12" back from the tip of the index finger on both arms. The 20% 2-tridecanone was not applied as uniformly as the other repellents because an insufficient quantity was available. Latex gloves were worn over the hands and replaced before each biting count. The control consisted of a soap wash, rinse and 25% ethanol swab and was conducted by the same person throughout the study. One-minute biting counts were recorded at 0, 1, 2, 4 & 6 hours post-treatment time intervals. All treatments were randomly assigned to each tester, two treatments per tester. Cage placement was also randomized at the beginning of each day of testing. Testers were rotated each day so that by the end of the study they had occupied each cage location. Each repellent was tested two times by three testers so that mean biting counts were based on six observations. A Hobo datalogger was used to monitor temperature and humidity throughout the study.

A balanced incomplete block design following American Society for Testing and Materials standards E 939-94 was employed. Data were normalized by square root transformation and submitted to analysis of variance and mean separation procedures via SS PC. Microsoft Excel 2000 pivot tables and charting functions were used to plot mean biting counts and standard errors by species and time interval for each treatment and control. Mean biting counts were transformed to percent protection or repellency by the following formula: Control−Treatment/Control×100.

TABLE 4

Mosquito counts in cages post-testing.

| | Total No. Dead/Escaped Females | Total No. Females Recovered | Total No. Females | Total No. Males Recovered | Total No. Males & Females |
|---|---|---|---|---|---|
| *Cx. quinq.* Cage No. | | | | | |
| 1 | 25 | 103 | 128 | 33 | 161 |
| 2 | 28 | 94 | 122 | 118 | 240 |
| 3 | 20 | 119 | 139 | 40 | 179 |
| 4 | 26 | 91 | 117 | 74 | 191 |
| *Ae. albopictus* Cage No. | | | | | |
| 1 | 23 | 56 | 79 | 13 | 92 |
| 2 | 23 | 28 | 51 | 11 | 62 |
| 3 | 26 | 72 | 98 | 17 | 115 |
| 4* | 18 | 9 | 27 | 2 | N/A |

*stockinette came loose after the study was completed and several mosquitoes escaped prior to post-test count.

Results and Discussion

Environmental conditions inside the laboratory where the study was conducted remained relatively constant throughout the 4-day test period (Table 5).

TABLE 5

Temperature and humidity during study.

| | Temperature | | | Relative Humidity (%) | | |
|---|---|---|---|---|---|---|
| Date | Average | High | Low | Average | High | Low |
| 07-Aug | 77.0 | 80.1 | 74.5 | 58.1 | 61.1 | 56.4 |
| 08-Aug | 77.2 | 78.7 | 74.5 | 56.2 | 59.5 | 53.8 |
| 09-Aug | 76.3 | 78.7 | 74.5 | 57.2 | 58.5 | 55.4 |
| 10-Aug | 76.0 | 76.6 | 75.2 | 55.3 | 60.6 | 51.7 |

Analysis of variance of square root x+1 transformed biting counts indicated highly significant differences between species. Analysis of variance performed by species showed highly significant (p<0.001) differences by date, time, tester, date*tester, treatment and date*treatment for both species. Mean separation tests showed significantly (p=0.05) higher counts in the control and significantly (p=0.05) lower counts with the 14% OFF!™ compared to the 2-undecanone and 2-tridecanone repellents for *Cx. quinquefasciatus*. The same held true for *Ae. albopictus*, except there was an additional significant difference between the 20% formulations (i.e., 2-undecanone and 2-tridecanone) and the 5% formulation. The 5% 2-undecanone formulation resulted in a significantly (p=0.05) lower mean biting count than the other two formulations. As anticipated, the tester performing the control treatment had significantly (p+0.05) more bites than the repellent testers irrespective of the species. There was no significant difference in bites among the three repellent testers for *Cx. quinquefasciatus*. Tester no. 3 (Tom) was found to have significantly (p=0.05) fewer bites than the other testers for Ae. albopictus. Significant differences (p=0.05) were also found between days and time intervals for both species. This was expected as the mosquitoes aged.

Figure 2:
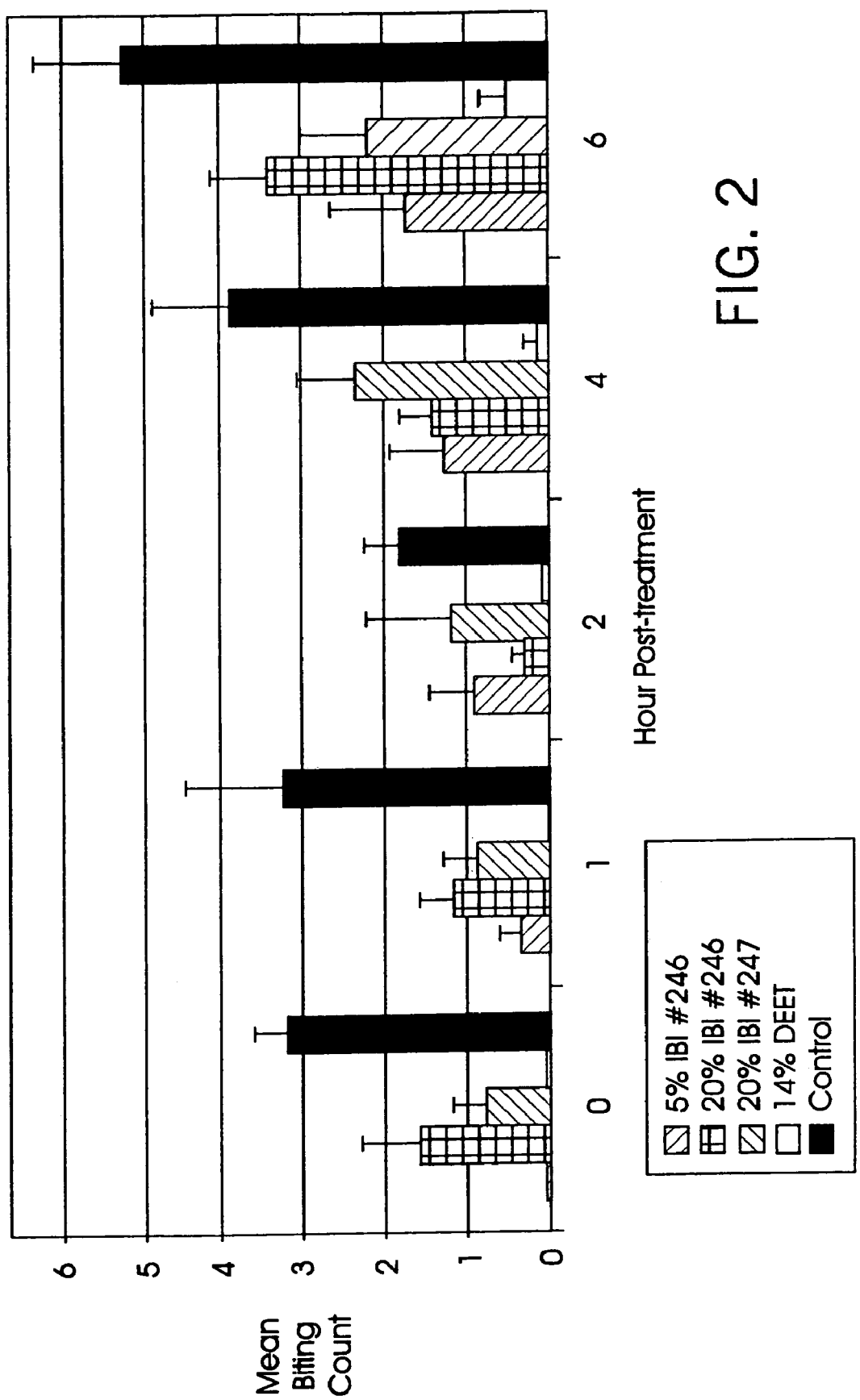
FIG. 2 presents the mean biting count and standard error by time interval post-treatment for *Aedes albopictus* (Average biting count and standard error for three formulations (5% 2-undecanone (IBI-246), 20% 2-undecanone (IBI-246), 20% 2-tridecanone (IBI-247)) versus DEET and a non-treated control over five time intervals.

The mean biting count and standard error by time interval post-treatment is presented for *Cx. quinquefasciatus* in FIG. 1 (Average biting count and standard error for three formulations (5% 2-undecanone (IBI-246), 20% 2-undecanone (IBI-246), 20% 2-tridecanone (IBI-247)) versus DEET and a non-treated control over five time intervals: *Culex quinquefasciatus*), and for *Ae. albopictus* in FIG. 2 (Average biting count and standard error for three formulations (5% 2-undecanone (IBI-246), 20% 2-undecanone (IBI-246), 20% 2-tridecanone (IBI-247)) versus DEET and a non-treated control over five time intervals: *Aedes albopictus*). Biting activity for *Cx. quinquefasciatus* increased in treatments and controls with increasing hours post-treatment (FIG. 1). This was attributed to time transpired since last sugar-water feeding. A somewhat similar trend occurred with *Ae. albopictus* although it was not as pronounced, particularly in earlier biting counts (FIG. 2). The controls exceeded the treatments at all biting count time intervals for both species. Biting activity was consistently greater for *Cx. quinquefasciatus* than *Ae. albopictus* because stocking rate was higher for the former species. *Cx. quinquefasciatus* bit at a much greater rate than expected.

Figure 3:
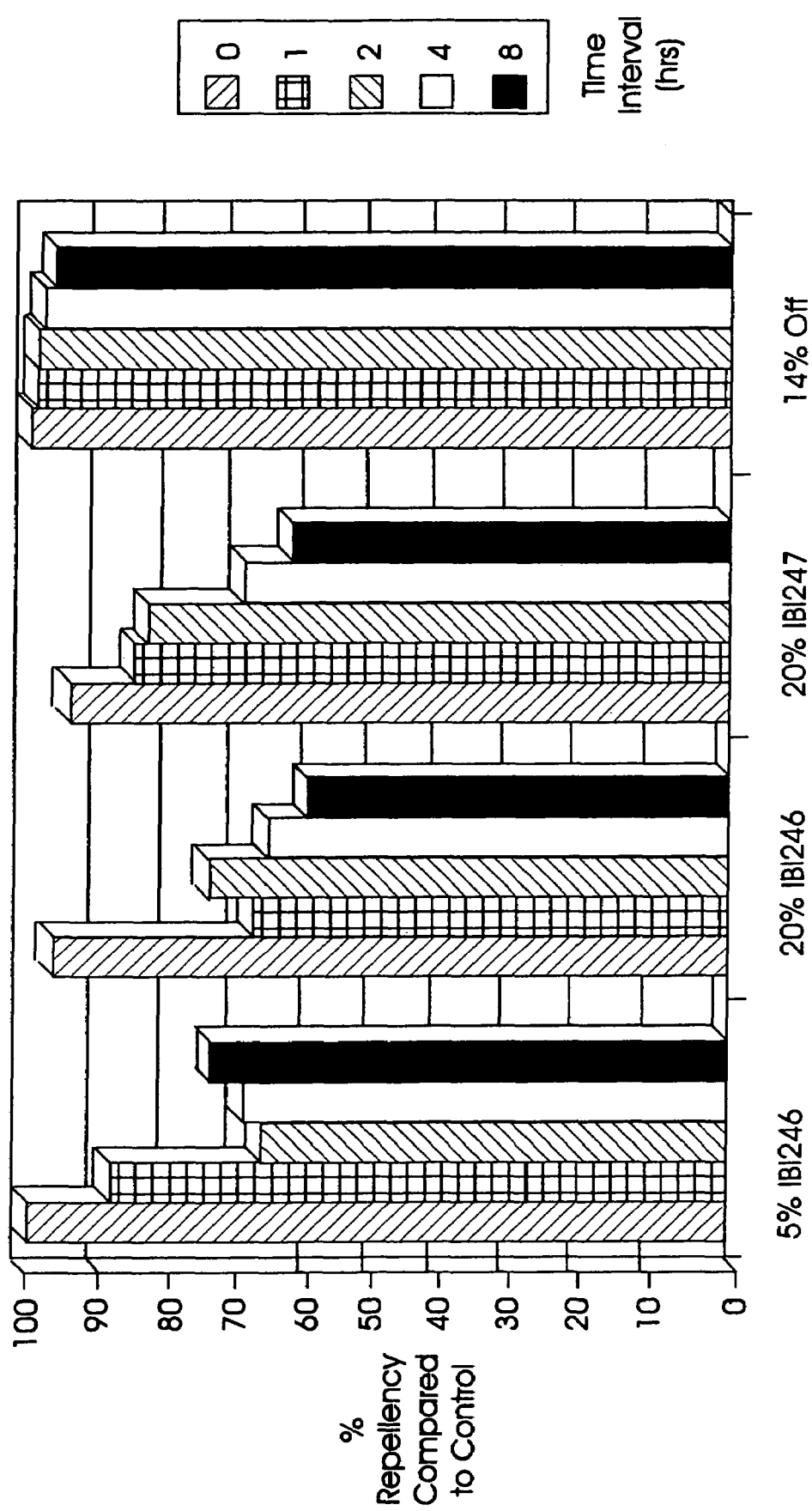
FIG. 3 provides percent protection/repellency for 2-undecanone and 2-tridecanone formulations and a commercial DEET product against *Cx. quinquefasciatus*.
Figure 4:
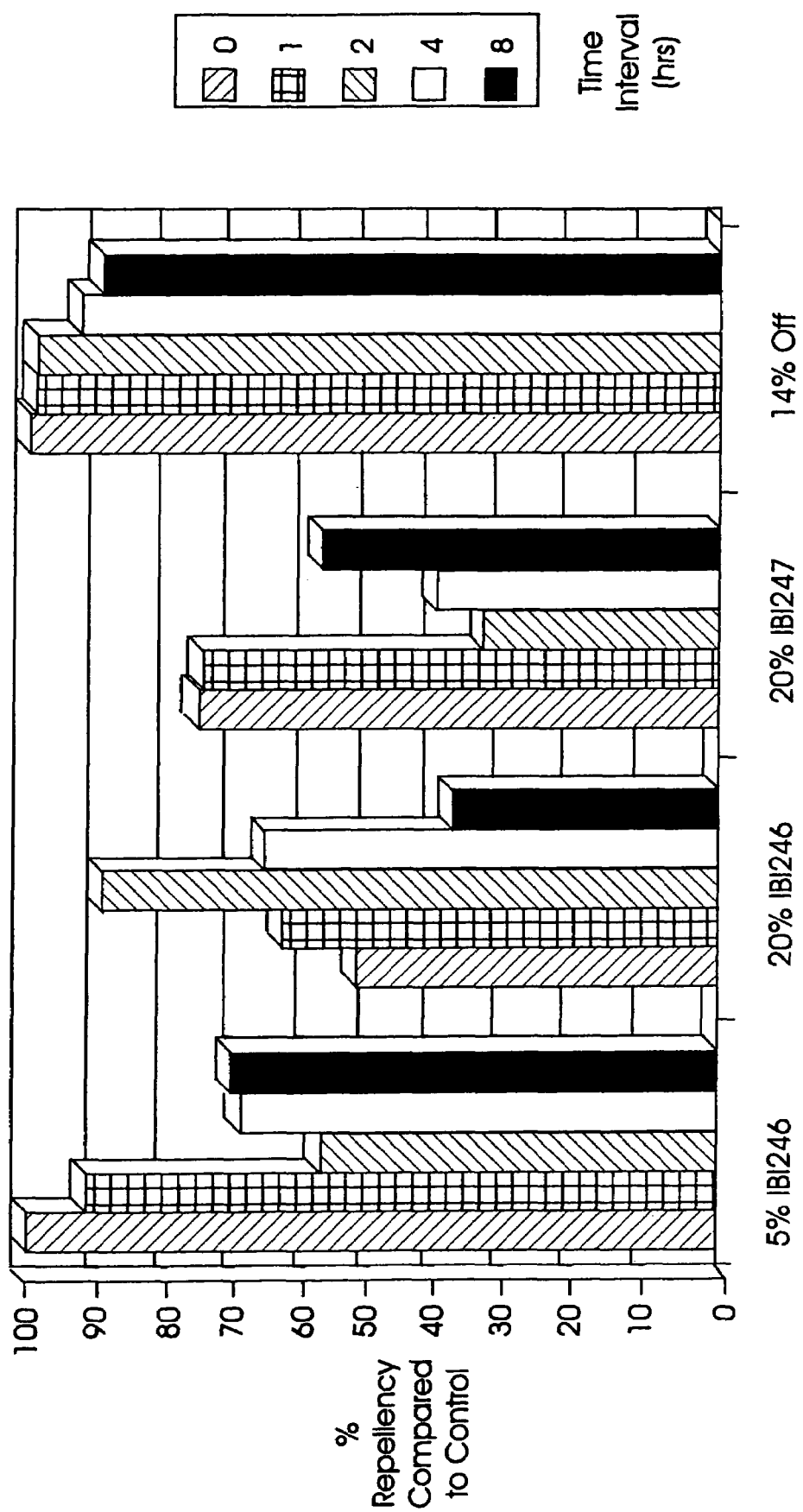
FIG. 4 provides percent protection/repellency for formulations of the invention and a commercial DEET formulation against *Ae. albopictus*.

All repellents initially performed well for *Cx. quinquefasciatus* during the 0 hour post-treatment biting count taken about 15 minutes after application (FIG. 3; (Percent protection/repellency for 2-undecanone and 2-tridecanone formulations and Off!™ against *Cx. quinquefasciatus*). Only Off!™ And 5% 2-undecanone worked well during the first biting count for *Ae. albopictus* (FIG. 4; Percent protection/repellency for IBI formulations and Off!™ against *Ae. albopictus*). As hours post-treatment increased there was a noticeable increase in biting activity for both species for 2-undecanone and 2-tridecanone repellents compared to Off!™ Compared to the controls, Off!™ provided 1.00% protection through 2 hours post-treatment for both species and >90% and >95% repellency out to 6 hours for *Ae. albopictus* and *Cx. quinquefasciatus*, respectively (FIGS. 3 and 4). The 2-undecanone and 2-tridecanone repellents gradually diminished in effectiveness from >95% repellency during the 0 hour biting count to 60-74% repellency at 6 hours post-treatment for *Cx. quinquefasciatus*. For *Ae. albopictus* repellency diminished from 100% to the upper 60 percentile for the 5% 2-undecanone formulation. The other two 2-undecanone and 2-tridecanone formulations fluctuated considerably and provided low repellency at post-treatment time intervals for *Ae. albopictus*. This was expected for the 20% 2-tridecanone repellent since formulation was used up prior to completing the experiment.

Protection provided by the 2-undecanone and 2-tridecanone repellents was not as complete as found with the commercial DEET product Off!™. This was probably attributable to formulation differences. The 2-undecanone and 2-tridecanone repellents were mixed in ethanol and probably evaporated more rapidly from the skin than Off!™. The 5% 2-undecanone repellent provided excellent initial repellency, rivaling or surpassing most of the other DEET alternatives tested.

EXAMPLE 8

Mosquito Repellency of 2-Undecanone Versus DEET Against *Culex* spp.

2-undecanone was dissolved in ethyl alcohol (v/v at 5% and 20%) and approximately 1 ml was sprayed onto cloth that was then wrapped around the investigator's forearm prior to insertion into a 59 cm×55 cm×59 cm mosquito cage containing approximately 100 *Culex* spp. adult mosquitoes. DEET was a formulated, commercial product (Cutter). The number of mosquito landings in 5 minutes was recorded as well as the overall behavior response of the mosquitoes. The results evidence repellency of 2-undecanone for mosquitoes, with the strongest effect at the 20% and 5% concentrations. The most impressive evidence of this repellent effect was the observation that the mosquitoes immediately disperse away from the treated arm and actually stop flying, instead lining up on the wire screen of the cage.

Figure 5:
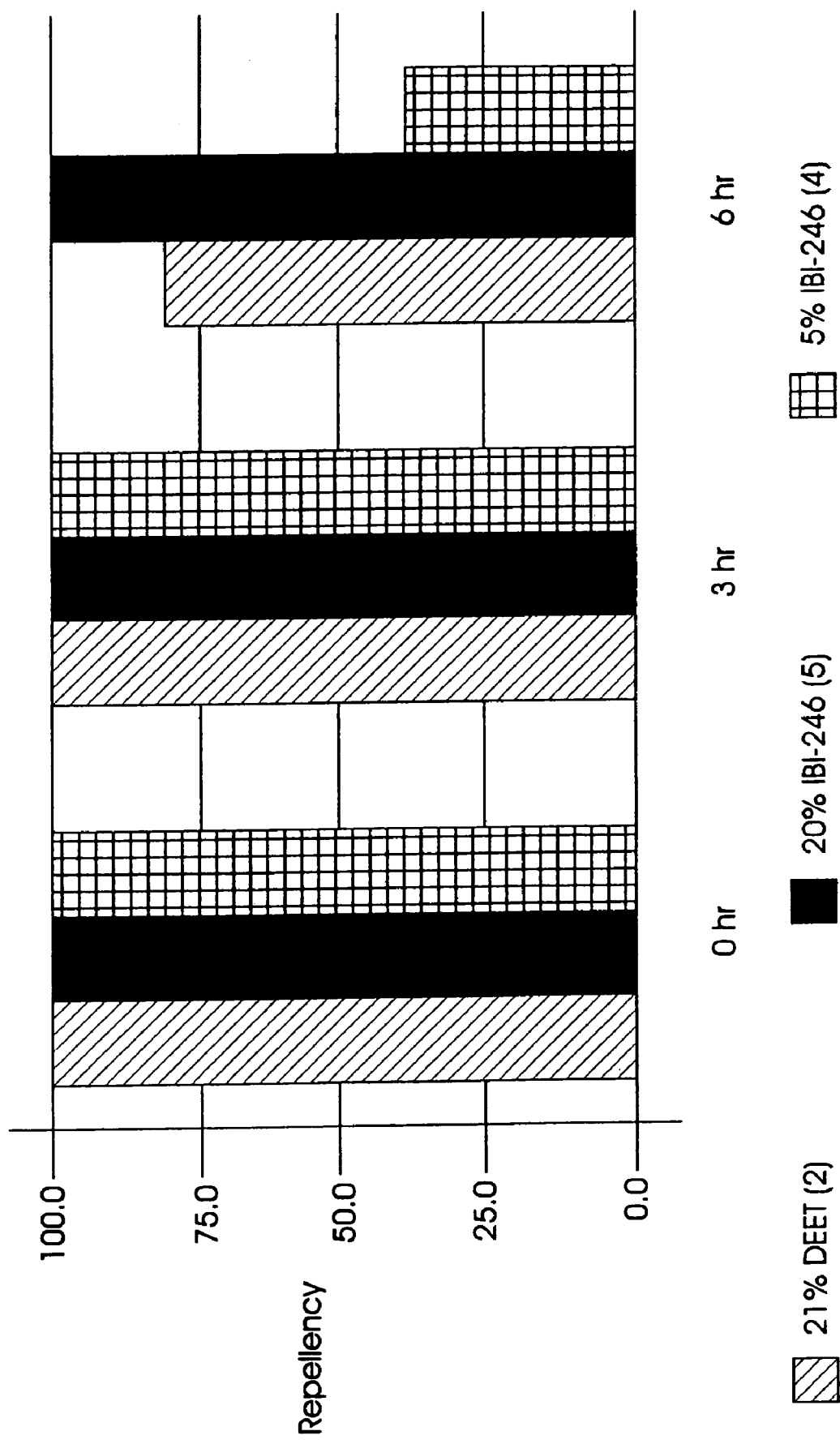
FIG. 5 presents a graph of repellency as a function of time for 0 hr, 3 hr and 6 hr post-application of the formulations (i) 21% DEET, (ii) 20% 2-undecanone (IBI-246) and (iii) 5% 2-undecanone.

The results are shown in FIG. 5 as a graph of repellency as a function of time for 0 hr, 3 hr and 6 hr post-application of the formulations (i) 21% DEET, (ii) 20% 2-undecanone (IBI-246) and (iii) 5% 2-undecanone (IBI-246), where repellency={[(# mosquito landings in Control test/# mosquitoes present in Control)−(# mosquito landings in Experiment/# mosquitoes present in Experiment)] divided by (# mosquito landings in Control test/# mosquitoes present in Control)}× 100.

EXAMPLE 9

Mosquito Repellency of 2-Undecanone

Versus DEET and Citronella Against *Aedes aegypti*

Tests were done with formulations of 2-undecanone and two commercial repellents, DEET and Citronella, to evaluate immediate and residual efficacy against mosquitoes, *Aedes aegypti*, for up to 24 hours. The formulation of 2-undecanone consisted of the compound dissolved in mineral oil. Another formulation was made up in the form of a lotion, and the compound exhibited good formulation behavior for lotion preparation.

The mineral oil-based formulation of 2-undecanone was then tested against the DEET and Citronella formulations.

Treatments were applied directly to the hand and arm of the investigator prior to exposure to the mosquitoes in an emergence cage. Controls were done with the carrier only. 2-undecanone showed excellent immediate and strong residual efficacy for up to 12 hours when applied at a 20% concentration in mineral oil, exceeding the efficacy of DEET (20%) and Citronella. However, residual activity was reduced, persisting up to 12 hours at the 5% level but none after 3 hours at the 1% concentration. The efficacy of Citronella was much less than either 2-undecanone or DEET.

Materials and Methods

Cages. Two mosquitoes cages were used for this experiment. The cages were constructed using wood framing and fine mesh wire screen. The dimensions of each cage were 59 cm high×55 cm wide by 59 cm deep. A hinged access door was installed at the front of each chamber for insertion of the water-filled containers filled with mosquito larvae. Also present at the front of each chamber was a 9 cm (I.D.) diameter plastic tube for insertion of the arm of the investigator. The arm insertion tube was sealed with a rubber stopper when not in use.

Mosquitoes and Mosquito Rearing. Mosquitoes (*Aedes aegypti*) were obtained as eggs from Dr. Gary Benzon (Benzon Research, Inc., Carlisle, Pa. 17013, USA) and allowed to hatch at three successive intervals so as to provide a continuing long-term supply of fresh insects. Following their arrival, the egg rafts were divided into approximately equal numbers in multiple water-filled containers within the test chambers, which also served as emergence cages. Following hatching, the larval cultures were fed with insect rearing compound supplied by United States Department of Agriculture, Gainesville, Fla., USA, courtesy of Mr. James Thomas. The water in the breeding chambers was changed regularly at two or three day intervals by filtration to minimize contamination and prevent overcrowding. Mosquitoes were bred throughout the 3-week study period in order to maintain a continuing supply of fresh insects (see below) and build up the population, usually exceeding 100 insects per cage.

Test Compounds and Testing Schedule. Testing was done with the mineral oil formulation of 2-undecanone for repellent activity by treating one arm of the investigator with approximately 1 ml of the test formulation. To avoid excessive bites and development of severe allergic reactions from multiple mosquito bites, treatments were applied to removable strips of cotton cloth taped to all parts of the investigator's hand and arm. Treatments were applied in a separate room, far from the mosquito cages. Following several minutes for the oil to soak in place, the cloth strips saturated with the treatment solution was attached to the investigator's wrist. Then, the treated arm was inserted through the insertion tube for 5 minutes. The other arm was treated with mineral oil (control) or a different compound and inserted into the insertion tube of the adjacent chamber. Next, the behavior of the mosquitoes in response to the presence of the investigator's arms was noted. Mosquito behavior was recorded as 1) landing or attempting to land on the investigator's hand or arm; 2) biting and sucking blood; or 3) dispersal away from the treated hand and arm towards the opposite ends of the cage. The approximate number of mosquitoes present in the cage at the beginning of each observation was noted. Treatments were alternated between the different cages. Each observation was repeated 3 times.

2-undecanone, DEET and Citronella arrived as liquids mixed in mineral oil in sealed plastic vials. To prepare the compounds for testing, the stocks were shaken vigorously to thoroughly mix the compounds in the mineral oil carrier, the vials opened and 1 ml samples applied directly as described above.

Observations. Mosquitoes were recorded as 1) repelled if they dispersed away from the treated hand/arm, changed course while in flight after approaching the treated hand/arm, touched the treated hand/arm and quickly withdrew; versus 2) not repelled if they landed on the treated hand/arm and remained on the cloth or skin of the investigator, or bit the investigator and sucked blood. The number of bites during the exposure period also was recorded.

Results

Testing commenced following rearing of the mosquitoes from eggs and continued over a 2½ week observation period as insects emerged from pupae held in water containers in the cages. The cages thereby served as emergence containers, allowing a continuing supply of large numbers of mosquitoes for testing. To provide a steady supply of fresh insects, rafts of eggs were immersed in water at different intervals over a 10-day period. However, numbers also varied considerably due to periodic deaths before new mosquitoes emerged. Initially, numbers ranged from under 50 mosquitoes per cage. Gradually, this increased and at the peak there were almost 200 mosquitoes per cage. As a result, some tests were done with smaller numbers of mosquitoes present than other tests. To increase survival, the cages were wrapped in clear plastic so as to elevate the relative humidity, which was checked periodically with a humidistat.

Table 6 presents the actual observations and calculates the percent of mosquitoes responding. The mineral oil controls established the base-line averages for use in comparing repellent activity for the five different observation periods. For the controls, the mean percent of landings on the treated hand/arm were 57.0, 50.1, 68.4, 63.9 and 56.4% for the 0, 3, 6, 9 and 12 hour observation periods. Mosquitoes that bit the hand/arm were noted with an asterisk. The occurrence of frequent bites was denoted with a double asterisk. Some mosquitoes bit the investigator's hand/arm in each of the 5 observation periods and in many instances the numbers were too numerous to count. Many drew blood. The mosquitoes appeared extremely excited and there was an intense buzzing, easily detectable when close to the cage.

Observations with 2-undecanone showed strong repellent activity. At zero hours, few mosquitoes approached and those that touched the hand or arm quickly left. None attempted to feed. Subsequently, at 3, 6 and 9 hours, the numbers of mosquitoes that approached and landed increased, but again the effect was the same, i.e., they touched the skin but quickly departed without attempting to feed. By 12 hours, however, some mosquitoes began biting, drew blood and one fed to completion.

Observations with DEET showed strong repellent activity, similar to that observed for 2-undecanone. At zero hours, virtually no mosquitoes attempted to land and only one bite was recorded. However, in contrast to the observations with 2-undecanone, the number of mosquitoes that attempted to land accelerated more rapidly within as little as 3 hours, and this increased by 6 and 9 hours. There was one bite at 6 hours and 2 bites by 9 hours after the compound was applied to the skin. At 12 hours, landings increased and the number of bites or attempted bites increased greatly. A total of 22 bites were recorded at 12 hours.

Observations with Citronella showed very weak repellent activity at zero hours, with numerous landings and many bites. Mosquitoes hovered in a veritable cloud buzzing around the treated hand and arm. Mosquito attacks accelerated at the later intervals, with even more bites. A total of 27 bites were recorded at 3 hours. Bites or attempted bites were too numerous to count at the later intervals, indicating very weak repellent activity.

Table 7 calculates the efficacy found at the five different time intervals for each of the compounds at the three different concentrations, 10%, 5% and 1% and for DEET. Efficacy was calculated according to the formula:

Efficacy=[(no.landings/no.present in control)−(no.landings/no. present in experimental) divided by (no.landings/no.present in control)]×100.

TABLE 6

Summary of observations for repellent activity of test compounds against mosquitoes.

| | Hours after treatment | | | | | | | | | |
|---|---|---|---|---|---|---|---|---|---|---|
| | 0 hours | | 3 hours | | 6 hours | | 9 hours | | 12 hours | |
| Rep | NP | NL | NP | NL | NP | NL | NP | NL | NP | NL |

6.1. Mineral Oil Control

| | | | | | | | | | | |
|---|---|---|---|---|---|---|---|---|---|---|
| 1 | 23** | 40 | 69** | 127 | 104** | 148 | 36** | 62 | 71** | 121 |
| 2 | 12* | 22 | 53** | 107 | 121** | 185 | 38** | 56 | 91** | 118 |
| 3 | 15** | 26 | 42** | 94 | 111** | 158 | 43** | 65 | 62** | 105 |
| Mean | 16.7 | 29.3 | 54.7 | 109.3 | 112.0 | 163.7 | 39.0 | 61.0 | 64.7 | 114.7 |
| Percent | | 57.0 | | 50.1 | | 68.4 | | 63.9 | | 56.4 |

Comments: Asterisk indicates bites or attempted bites. Double asterisk indicates multiple bites during the same observation period. Numerous mosquitoes hovered around the hand/arm, typically 15-20, occasionally even greater numbers were flying with frequent visits to the arm/hand. Mosquitoes were extremely excited and a distinct buzzing sound was heard throughout the cage when mosquito numbers were high.

6.2. 20% 2-Undecanone in Mineral Oil

| | | | | | | | | | | |
|---|---|---|---|---|---|---|---|---|---|---|
| 1 | 2 | 36 | 1 | 58 | 24 | 385 | 6 | 40 | 4* | 65 |
| 2 | 0 | 31 | 6 | 85 | 21 | 165 | 1 | 33 | 8 | 55 |
| 3 | 2 | 44 | 4 | 78 | 29 | 155 | 7 | 46 | 11* | 70 |
| 4 | 2 | 195 | — | | — | | — | | — | |
| 5 | 3 | 168 | — | | — | | — | | — | |
| 6 | 5 | 177 | — | | — | | — | | — | |
| Mean | 2.3 | 108.5 | 3.7 | 73.7 | 24.7 | 168.3 | 4.7 | 39.7 | 7.7 | 63.3 |
| Percent | | 2.0 | | 5.0 | | 14.7 | | 11.8 | | 12.2 |

Comments: The 2-undecanone formulation was highly repellent. At zero hours, all of the mosquitoes dispersed to the opposite sides of the cage away from the treated arm/hand, and almost all stopped flying within less than 1-2 minutes. Landings observed were very brief, mostly to the finger tips or underside of hand where the repellent was not as concentrated. Mosquitoes landed, walked around on skin for 1-

TABLE 6-continued

Summary of observations for repellent activity
of test compounds against mosquitoes.

| | Hours after treatment | | | | | | | | | |
|---|---|---|---|---|---|---|---|---|---|---|
| | 0 hours | | 3 hours | | 6 hours | | 9 hours | | 12 hours | |
| Rep | NP | NL | NP | NL | NP | NL | NP | NL | NP | NL |

2 seconds, and then flew off. No bites were observed until 12 hours. There were 4
bites at 12 hours, one of which filled with blood to completion. Strong avoidance
response was still evident through 12 hours. Odor was very strong until 6 hours, and
weaker but still detectable at 12 hours.
6.3. 20% DEET in Mineral Oil

| 1 | 3* | 63 | 22 | 185 | 31* | 133 | 11* | 81 | 16* | 155 |
|---|---|---|---|---|---|---|---|---|---|---|
| 2 | 1 | 66 | 11 | 78 | 21 | 140 | 7 | 72 | 37** | 185 |
| 3 | 1 | 60 | 23 | 165 | 13 | 121 | 4* | 79 | 33** | 190 |
| 4 | 3 | 160 | — | | — | | — | | — | |
| Mean | 2.0 | 87.3 | 18.7 | 142.7 | 21.7 | 131.3 | 7.3 | 77.3 | 28.7 | 176.7 |
| Percent | | 2.3 | | 13.1 | | 16.5 | | 9.4 | | 16.2 |

Comments: The DEET formulation was highly repellent. When applied at zero
hours, almost all of the mosquitoes dispersed to the opposite sides of the cage away
from the treated arm/hand, and almost all stopped flying within less than 1-2
minutes. Few landings were observed all were very brief, just a touchdown and fly
off. Repellent effect appeared to diminish after 6 hours, with increased landings and
a few bites. There was 1 bite at 6 hours, 2 bites at 9 hours, 22 bites at 12 hours.
The repellent effect diminished considerably by 12 hours with a great increase in
the number of bites.
6.4. 20% Citronella in Mineral Oil

| 1 | 21* | 98 | 16* | 45 | | | 37* | 133 | | |
|---|---|---|---|---|---|---|---|---|---|---|
| 2 | 24* | 115 | 24** | 66 | | | 62** | 168 | | |
| 3 | 28** | 108 | 31** | 83 | | | 44** | 142 | | |
| Mean | 24.3 | 107 | 23.7 | 64.7 | | | 47.7 | 147.7 | | |
| Percent | | 22.7 | | 36.7 | | | | 32.3 | | |

Comment: Very weak repellent activity was observed. There were numerous
landings and 5 bites at zero hour. By 9 hours, there was a virtual cloud of
mosquitoes hovering over treated hand/arm, biting or attempting to bite. Bites
were too numerous to count.

Rep = Replicate;
NP = number present;
NL = number landing

TABLE 7

Repellent efficacy of 2-undecanone in mineral oil (20%) versus
DEET and Citronella against mosquitoes Aedes aegypti.
Percent Efficacy Post-Treatment

| Compound | 0 hours | 3 hours | 6 hours | 9 hours | 12 hours |
|---|---|---|---|---|---|
| 2-Undecanone (20%) in mineral oil | 96.5 | 90.1 | 78.5 | 81.5 | 78.4 |
| DEET (20%) | 96.0 | 73.9 | 75.9 | 85.3 | 71.3 |
| Citronella (20%) | 60.2 | 26.8 | — | 52.8 | — |

Efficacy was calculated according to the formula: Efficacy = [(no. landings/no. present in control) − (no. landings/no. present in experimental) divided by (no. landings/no. present in control)] × 100.

INDUSTRIAL APPLICABILITY

The method, compounds and formulations of the present invention are useful to repel insect pests from a subject or substrate. For example, compoimds of Formula (I) and formulations thereof can be applied to a human or animal subject, or an article appurtenant to such subject, e.g., a garment or fixture in the environment of the subject, for repelling mosquitoes and/or ticks. The animal subject may be a mammalian subject, such as horses, cows, sheep, dogs, cats, or other livestock or household pet. The compounds and formulations of the invention afford an effective alternative to the use of N,N-diethyl-meta-toluamide (DEET) repellants.

That which is claimed is:

1. A method of repelling an insect pest, comprising applying to a subject an active compound in an amount effect to repel said insect pest;
   wherein said insect pest is selected from the group consisting of ticks and mosquitoes;
   and wherein said active compound is selected from the group consisting of 2-tridecanone, 2-undecanone, and mixtures thereof.

2. A method according to claim 1, wherein said insect is a mosquito.

3. A method according to claim 1, wherein said insect is an *Anopheles, Aedes,* or *Culex* mosquito.

4. A method according to claim 1, wherein said insect is a tick.

5. A method according to claim 1, wherein said insect is a tick selected from the group consisting of *Ornithodoris parkeri* and the American dog tick.

6. A method according to claim 1, wherein said applying step is carried out by topically applying said active compound to the skin of said subject.

7. A method according to claim 1, wherein said applying step is carried out by applying said active compound to an article, which article is worn by a subject.

8. A method according to claim 1, wherein said active compound is 2-tridecanone.

9. A method according to claim 1, wherein said active compound is 2-undecanone.

10. A method of repelling mosquitoes from a human subject, comprising applying to skin of said human subject, or to a garment article worn by said human subject, an effective amount of a repellant comprising 2-undecanone.

11. A method of repelling mosquitoes from an animal subject, comprising applying to said animal subject, or an article appurtenant to said animal subject, an effective amount of a repellant comprising 2-undecanone.

12. The method of claim 11, wherein the animal subject is a livestock animal.

13. The method of claim 11, wherein the animal subject is a household pet.

14. The method of claim 11, wherein the animal subject is a mammal.

15. The method of claim 11, wherein the animal subject is selected from the group consisting of horses, cows, sheep, dogs, and cats.

16. A method of repelling mosquitoes and ticks from a subject, comprising applying to said subject, or an article appurtenant to said subject, an effective amount of a repellant comprising 2-undecanone.

17. The method of claim 16, wherein said subject is selected from the group consisting of human subjects and non-human mammalian subjects.

18. The method of claim 16, wherein the repellant is in a spray or lotion form, and said applying step comprises applying the repellent to the skin of the subject.

19. The method of claim 16, wherein the repellant is in a spray form, and said applying step comprises applying the repellent to the skin of the subject.

20. The method of claim 16, wherein the repellant is in a lotion form, and said applying step comprises applying the repellent to the skin of the subject.

* * * * *

UNITED STATES PATENT AND TRADEMARK OFFICE
CERTIFICATE OF CORRECTION

PATENT NO.         : 7,288,573 B2                              Page 1 of 1
APPLICATION NO. : 10/486632
DATED              : October 30, 2007
INVENTOR(S)        : Roe It is certified that error appears in the above-identified patent and that said Letters Patent is hereby corrected as shown below:

On Title Page:
Item (22):  Please correct "PCT Filed:  Feb. 14, 2002"
            To read -- PCT Filed:  March 14 2002 --

Column 1, Line 9:  Please correct "commonly owned"
            To read -- of commonly owned --

Column 13, Line 24:  Please correct "23. 50% IBI-246"
            To read -- 2.3. 50% IBI-246 --

Column 24, Claim 1, Line 49:  Please correct "effect to repel"
            To read -- effective to repel --

Signed and Sealed this

Thirteenth Day of May, 2008

JON W. DUDAS
*Director of the United States Patent and Trademark Office*